United States Patent
Bodner et al.

(10) Patent No.: US 8,249,719 B2
(45) Date of Patent: Aug. 21, 2012

(54) LEAD STABILIZER WITH RETENTION FEATURES

(75) Inventors: Jeffrey P. Bodner, St. Paul, MN (US); Brendan E. Koop, Coon Rapids, MN (US); Kurt S. Aschenbeck, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/265,273

(22) Filed: Nov. 5, 2008

(65) Prior Publication Data

US 2009/0125058 A1    May 14, 2009

Related U.S. Application Data

(60) Provisional application No. 60/986,918, filed on Nov. 9, 2007.

(51) Int. Cl.
    *A61B 17/00*    (2006.01)
(52) U.S. Cl. ............... 607/116; 606/232; 29/557
(58) Field of Classification Search .................. 607/116, 607/126; 29/557
    See application file for complete search history.

(56) References Cited

U.S. PATENT DOCUMENTS

| | | | |
|---|---|---|---|
| 4,266,552 A | 5/1981 | Dutcher et al. | |
| 4,276,882 A | 7/1981 | Dickhudt et al. | |
| 4,287,891 A | 9/1981 | Peters | |
| 4,387,727 A | 6/1983 | Sandstrom | |
| 4,437,475 A | 3/1984 | White | |
| 4,516,584 A | 5/1985 | Garcia | |
| 4,538,623 A | 9/1985 | Proctor et al. | |
| 4,553,961 A * | 11/1985 | Pohndorf et al. | 604/175 |
| 4,613,329 A | 9/1986 | Bodicky | |
| 4,615,472 A | 10/1986 | Nash | |
| 4,672,979 A * | 6/1987 | Pohndorf | 607/126 |
| 4,676,782 A | 6/1987 | Yamamoto et al. | |
| 4,683,895 A | 8/1987 | Pohndorf | |
| 4,768,523 A | 9/1988 | Cahalan et al. | |
| 4,906,233 A | 3/1990 | Moriuchi et al. | |
| 5,036,862 A | 8/1991 | Pohndorf | |
| 5,107,856 A | 4/1992 | Kristiansen et al. | |
| 5,129,405 A | 7/1992 | Milijasevic et al. | |
| 5,152,298 A | 10/1992 | Kreyenhagen et al. | |
| 5,242,431 A | 9/1993 | Kristiansen | |
| 5,257,975 A | 11/1993 | Foshee | |
| 5,273,053 A | 12/1993 | Pohndorf | |
| 5,376,108 A | 12/1994 | Collins et al. | |

(Continued)

OTHER PUBLICATIONS

"Suture Sleeve with Removable Fins", Technical Disclosure from www.ip.com, No. IPCOM000125732D, published Jun. 15, 2005, full document available at http://www.ip.com/pubview/IPCOM000125732D, 4 pages.

(Continued)

*Primary Examiner* — George Manuel
*Assistant Examiner* — Alyssa M Alter
(74) *Attorney, Agent, or Firm* — Faegre Baker Daniels LLP

(57) ABSTRACT

An anchoring device for anchoring a medical lead implanted in a patient includes a substantially elongate, hollow, tubular, and elastically compressible body. The body has a longitudinal axis, a groove formed circumferentially about the body for receiving a suture and an inner bore forming a recessed portion. The anchoring device also has a surrounding portion adjacent the recessed portion, where the recessed portion has increased retention characteristics on a medical lead relative to the surrounding portion of the inner bore.

19 Claims, 3 Drawing Sheets

U.S. PATENT DOCUMENTS

| | | | |
|---|---|---|---|
| 5,423,763 A | 6/1995 | Helland et al. | |
| 5,476,493 A | 12/1995 | Muff | |
| 5,549,619 A | 8/1996 | Peters et al. | |
| 5,584,874 A | 12/1996 | Rugland et al. | |
| 5,603,730 A | 2/1997 | Romkee | |
| 5,628,780 A | 5/1997 | Helland et al. | |
| 5,674,273 A | 10/1997 | Helland | |
| 5,683,403 A | 11/1997 | Adams et al. | |
| 5,683,446 A * | 11/1997 | Gates | 607/126 |
| 5,709,644 A | 1/1998 | Bush | |
| 5,735,891 A | 4/1998 | White | |
| 5,746,722 A | 5/1998 | Pohndorf et al. | |
| 5,824,032 A | 10/1998 | Belden | |
| 5,827,296 A | 10/1998 | Morris et al. | |
| 5,843,146 A | 12/1998 | Cross, Jr. | |
| 5,876,429 A | 3/1999 | Schroeppel | |
| 5,957,968 A * | 9/1999 | Belden et al. | 607/126 |
| 6,002,969 A | 12/1999 | Machek et al. | |
| 6,259,953 B1 | 7/2001 | Lucchesi et al. | |
| 6,473,654 B1 | 10/2002 | Chinn | |
| 6,554,802 B1 | 4/2003 | Pearson et al. | |
| 6,592,553 B2 | 7/2003 | Zhang et al. | |
| 6,901,287 B2 | 5/2005 | Davis et al. | |
| 6,921,295 B2 | 7/2005 | Sommer | |
| 6,985,777 B2 | 1/2006 | Tsuboi et al. | |
| 7,082,337 B2 | 7/2006 | Sommer et al. | |
| 7,184,841 B1 | 2/2007 | Bodner et al. | |
| 7,218,972 B2 | 5/2007 | Rodriguez | |
| 7,242,986 B2 | 7/2007 | Rodriguez | |
| 7,248,930 B1 | 7/2007 | Woloszko et al. | |
| 7,398,125 B2 | 7/2008 | Osypka et al. | |
| 2003/0050668 A1 | 3/2003 | Lee | |
| 2003/0195600 A1 | 10/2003 | Tronnes et al. | |
| 2003/0220678 A1 | 11/2003 | Tronnes et al. | |
| 2004/0059403 A1 | 3/2004 | Massullo | |
| 2004/0254623 A1 | 12/2004 | Rodriguez et al. | |
| 2005/0080470 A1 | 4/2005 | Westlund et al. | |
| 2005/0177220 A1 | 8/2005 | Iaizzo et al. | |
| 2006/0235484 A1 | 10/2006 | Jaax et al. | |
| 2006/0264803 A1 | 11/2006 | Lui et al. | |
| 2007/0078399 A1 | 4/2007 | Olson | |
| 2009/0125059 A1 | 5/2009 | Verzal et al. | |
| 2009/0125060 A1 | 5/2009 | Rivard et al. | |
| 2009/0125061 A1 | 5/2009 | Rivard et al. | |

OTHER PUBLICATIONS

"Pacing Lead Stabilizer with Modified Slit Geometry", Technical Disclosure from www.ip.com, No. IPCOM000130753D, published Nov. 3, 2005, full document available at http://www.ip.com/pubview/IPCOM000125732D, 6 pages.

* cited by examiner

LEAD STABILIZER WITH RETENTION FEATURES

CROSS REFERENCE TO RELATED APPLICATIONS

This application claims priority under 35 U.S.C. §119(e) to U.S. Provisional Patent Application No. 60/986,918, filed on Nov. 9, 2007, entitled "LEAD STABILIZER WITH RETENTION FEATURES," which is incorporated herein by reference in its entirety.

TECHNICAL FIELD

The present invention relates generally to anchoring devices for anchoring medical leads to tissue of a patient. More specifically, the present invention relates to anchoring devices having recessed lead retention features.

BACKGROUND

Medical leads are used in a variety of applications. In some uses, medical leads are anchored to a patient's tissue using anchoring devices, including those commonly referred to as "suture sleeves." For example, in many applications, an electrical lead connected to a cardiac rhythm management (CRM) device is secured to patient tissue at or near a vein entry site to help prevent both acute and chronic lead migration and dislodgement. In particular, leads are anchored, or retained, by securing a suture sleeve about the lead and suturing the suture sleeve to the patient's tissue.

SUMMARY

Some aspects of the invention are related to an anchoring device for anchoring a medical lead implanted in a patient, where the anchoring device includes a substantially elongate, hollow, tubular, and elastically compressible body. The body has a longitudinal axis, a groove formed circumferentially about the body for receiving a suture and an inner bore forming a recessed portion. The anchoring device also has a surrounding portion adjacent the recessed portion, where the recessed portion has increased retention characteristics on a medical lead relative to the surrounding portion of the inner bore. Related embodiment systems and methods are also contemplated.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
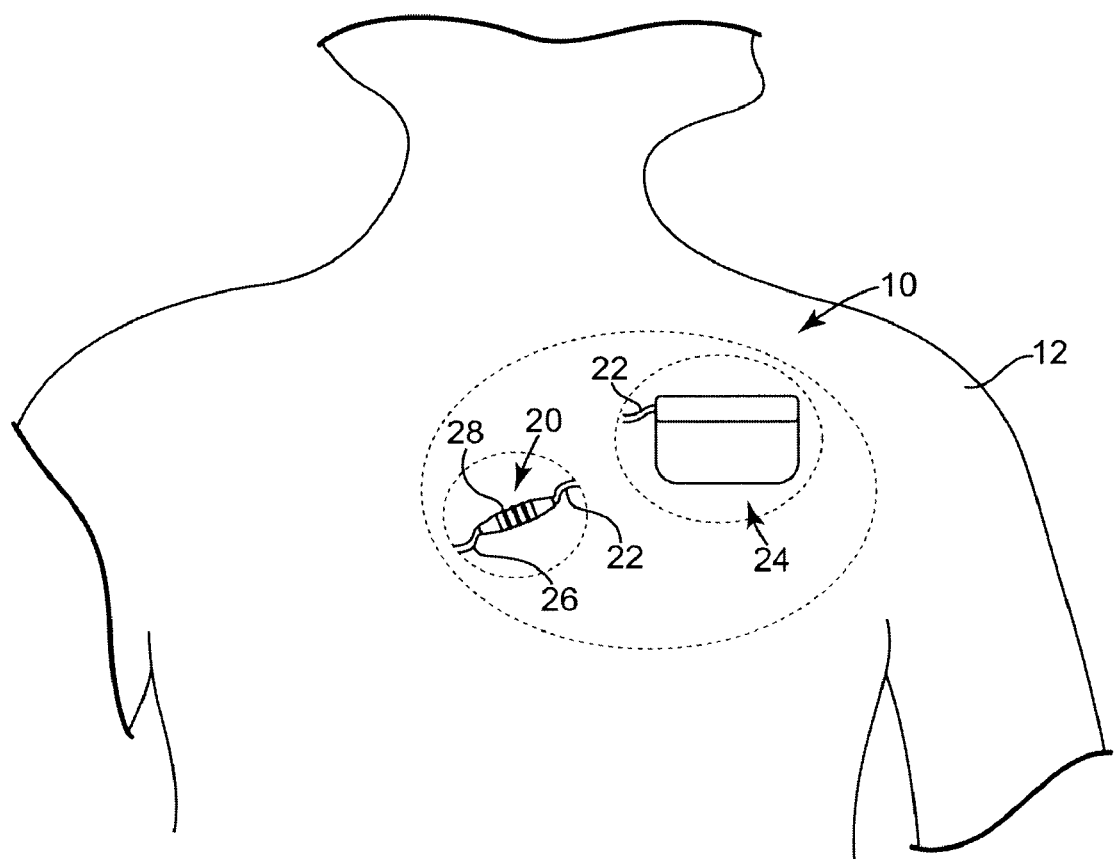
FIG. 1 is a schematic view of an implanted medical system, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an implanted medical system 10 implanted in a patient's body 12 according to various embodiments of the invention. The system 10 includes an anchoring device or suture sleeve 20, a lead 22, and an implanted medical device (IMD) 24 connected to the lead 22. In some embodiments, the IMD 24 is a cardiac rhythm management (CRM) device (e.g., a pacemaker or defibrillator) or other therapeutic device (e.g., a drug pump), implanted in the body 12.

In some embodiments, the lead 22 is an electrical lead of a type suitable for use with CRM devices, for example. The lead 22 includes an inner conductive coil (not shown) or other internal features and an outer, insulating sheath 26 extending over the internal features of the lead 22. In some embodiments, the lead 22 includes electrodes (not shown) or other features for stimulating or sensing functionality. The lead 22 is generally characterized by a maximum radial crushing force, or maximum compressive force, that the lead 22 can withstand prior to sustaining damage.

As shown in FIG. 1, and in general terms, the anchoring device 20 is positioned over the insulating sheath 26 of the lead 22 and serves to stabilize the lead 22 at or near a vein entry site (not shown) to help prevent both acute and chronic lead migration and dislodgement. In some embodiments, the anchoring device 20 is compressed onto the lead 22 using fasteners 28 (sutures as shown in FIG. 1) secured about the anchoring device 20. According to some methods, the fasteners 28 are manually secured about the anchoring device 20 by a physician using some tension or tying force. The tying force often varies from about 1 to about 8 pounds or more.

If the compressive forces caused by the fasteners 28 are sufficiently high, the conductive coils and/or insulative sheath 26 can be damaged by concentrated forces at interfaces between the lead 22 and the anchoring device 20 proximate the fasteners 28. Deformation of the conductive coils can reduce efficacy or even result in complete failure (e.g., shorting) of the lead 22. The lead 22 can also sustain damage to the insulating sheath 26, for example if the fasteners 28 cut through the anchoring device 20 and then into the insulating sheath 26. In turn, if the anchoring device 20 is not compressed onto the lead 22 with sufficient force, the lead 22 is not retained sufficiently within the device 20 for it to function properly. In general terms, the anchoring device 20 is adapted to address what is often a trade off between lead retention and the potential for crushing the lead 22 by increasing lead retention forces exhibited under lower compressive forces.

Although sutures in general, and manual methods of tying of sutures in particular, are referenced herein as embodying the fasteners 28 and use thereof, other fasteners and fastening methods, such as spring clips or automatic suture tying devices, for example, are also contemplated for compressing the device 20 onto the lead 22.

Figure 2:
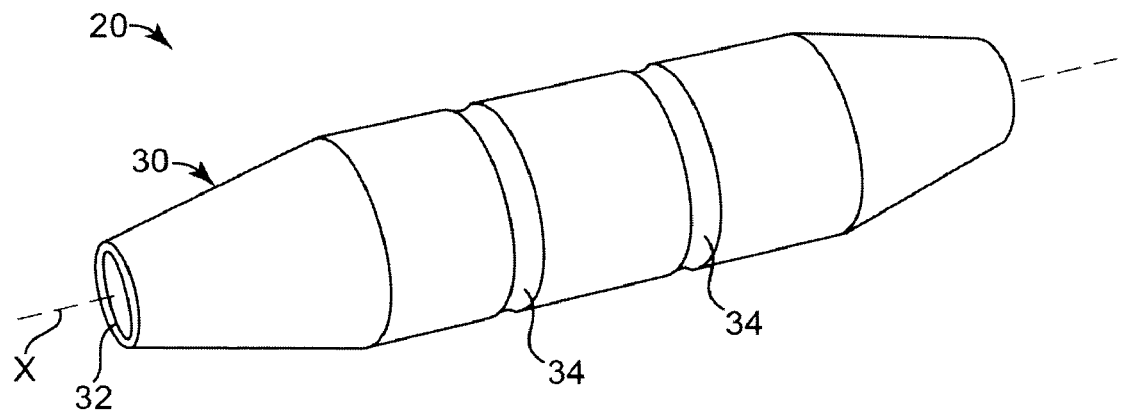
FIG. 2 is an isometric view of an anchoring device of the system of FIG. 1, according to some embodiments.

FIG. 2 shows an isometric view of the anchoring device or suture sleeve 20. In some embodiments, the anchoring device 20 is formed of an elastomeric material and has a generally flexible, substantially compliant, and elastically compressible body. For example, the device 20 may be formed of silicone or any of the numerous materials known in the art for forming suture sleeves.

As shown in FIG. 2, overall, the device 20 is substantially elongate, tubular, and tapered toward each end and defines a longitudinal axis X. The anchoring device 20 has an outer surface 30 and an inner bore 32 defining an inner diameter of the device 20. The inner bore 32 is configured, or otherwise sized and shaped, to receive and retain the lead 22 upon tying of the fasteners 28. The outer surface 30 has a plurality of circumferentially extending suture grooves 34 formed therein. As described in greater detail below, the inner bore 32 is adapted to facilitate retention of the lead 22 upon tightening the fasteners 28 (see FIG. 1).

The device 20 also optionally includes features such as longitudinal slots (not shown) for facilitating compression of the anchoring device 20 with the fasteners 28, compression governors (not shown) for limiting maximum compression of the device 20 on the lead 22, and other features, such as those described in the commonly owned U.S. patent applications identified by Attorney Docket Nos. 60/986,922, 60/986,911, and 60/986/915 entitled "PRE-SELECTED COMPRESSION LEAD ANCHORING DEVICE," "COMPRESSION CONTROL LEAD ANCHORING DEVICE," and "COMPRESSION MEMBER SUTURE SLEEVE," respectively, each of which were filed on even date herewith and the contents of each of which are incorporated herein by reference.

Figure 3:
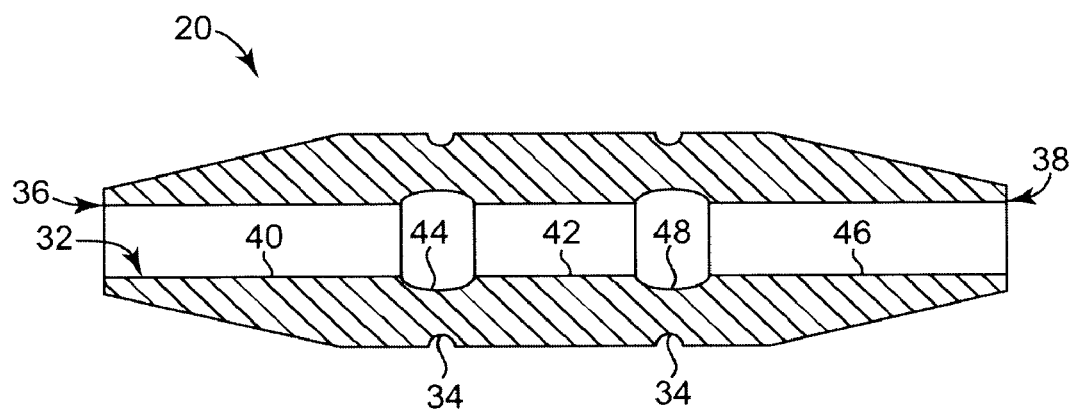
FIG. 3 is a cross-sectional view of the anchoring device of FIG. 2, according to some embodiments.

FIG. 3 is a cross-sectional view of the anchoring device 20 taken along the central longitudinal axis X shown in FIG. 2, showing the inner bore 32 of the anchoring device 20 in greater detail. The inner bore 32 extends in a substantially longitudinal fashion between the first and second ends 36, 38 and includes a first portion 40, a second portion 42, a first recessed portion 44 extending longitudinally between the first and second portions 40, 42, a third portion 46, and a second recessed portion 48 extending longitudinally between the second and third portions 42, 46. According to some embodiments, the device 20 has the two recessed portions 44, 48 and the three portions 40, 42, 46 located adjacent the recessed portions 44, 48 and surrounding the recessed portions 44, 48, although other embodiments include any number and combination of recessed portions and adjacent portions.

As shown in FIG. 3, the recessed portions 44, 48 define an increased bore diameter relative to each of the first, second, and third portions 40, 42, 46, respectively. The recessed portions 44, 48 extend circumferentially about the interior of the device 20 or are substantially circular in transverse cross-section. The recessed portions 44, 48 are also substantially arcuate or semi-circular when viewed along the longitudinal cross-section shown in FIG. 3. In some embodiments, the recessed portions 44, 48 form substantially concave features each generally positioned under a respective one of the suture grooves 34. According to other embodiments, the recessed portions 44, 48 take a variety of shapes (e.g., square) and are positioned at any number of locations. The first, second, and third portions 40, 42, 46 have substantially continuous diameters according to some embodiments, although any of a variety of tapers or other internal features are included as desired.

In some embodiments, one or both of the recessed portions 44, 48 define surface areas of at least about 10 square mm. In some embodiments, one or both of the recessed portions 44, 48 are recessed by about 0.3 to about 0.5 mm relative to the surrounding portions of the inner bore 32. Although examples of dimensions are provided above, other surface areas and relative amounts of recess are contemplated.

The recessed portions 44, 48 are adapted to engage the lead 22 with increased stiction relative to the first, second and third portions 40, 42, 46 once the device 20 has been compressed onto the lead 22 (FIG. 1). As used herein, "stiction" corresponds to the force required to cause one body in contact with another to begin to move. In particular, the recessed portions 44, 48 are adapted such that when they are compressed against the lead 22 the device 20 is transitioned from a first state exhibiting a first stiction characteristic to a second state exhibiting a second, higher stiction characteristic with the lead 22. Various means for providing such stiction enhancement are described below.

As one example of a stiction enhancing feature, in some embodiments, one or both of the recessed portions 44, 48 include a friction-enhancing coating or an anti-lubricous coating (not shown) deposited on the recessed portions 44, 48 of the inner bore 32 while the first, second, and third portions 40, 42, 46 are substantially free of or have substantially less of the friction-enhancing coating. Some friction enhancing coatings include adhesives, such as biocompatible pressure sensitive adhesives, binder systems with friction enhancing particulate, or others. As another example, the recessed portions 44, 48 optionally include embedded, friction-enhancing materials molded into the inner bore 32 at the recessed portions 44, 48.

In still other embodiments, one or both of the recessed portions 44, 48 are formed to have a very smooth surface finish which actually generates increased retention forces or stiction between the lead 22 and the device 20 once the recessed portions 44, 48 are compressed against the lead 22. In some embodiments, the recessed portions 44, 48 have a very smooth finish corresponding to a surface roughness about 15 microinches Ra (roughness average) or less. In other embodiments, the recessed portions 44, 48 have an ultra smooth finish corresponding to a surface roughness of about 5 microinches Ra or less. A variety of surface roughnesses for the recessed portions 44, 48 are contemplated, including a surface roughness from about 15 microinches to about 5 microinches Ra, for example, and others.

The relatively smoother surface finish actually increases stiction with the lead body by increasing mechanical, adsorption, electrostatic, or diffusive interactions between one or both of the recessed areas 44, 48 and the sheath 26 of the lead 22. For example, the smooth surface can result in increased contact surface area between the recessed areas 44, 48 and the lead 22. This increase in contact area can result in a relatively high tackiness or frictional adhesion between the device 20 and lead 22. The degree of increase in stiction is dependent upon a variety of factors, including surface roughness of the two bodies in contact, compressive force between the two bodies, and material properties of the two bodies, including material type, modulus of elasticity, and others. In one example, the recessed areas 44, 48 define uncoated, silicone surfaces and the lead sheath 26 defines a polyurethane or silicone surface, or a surface including other known lead materials.

In some embodiments, some or all of the first, second, and third portions 40, 42, 46 include a friction reducing coating or other surface treatment (not shown). For example, a lubricous surface treatment is optionally applied to one or all of the first, second, and third portions 40, 42, 46. In some embodiments, the lubricous surface treatment includes a siloxane derivative applied by chemical vapor deposition, such as that sold under the trade name "SILGLIDE" by APPLIED MEMBRANE TECHNOLOGY, INC. of Minnetonka, Minn. Additionally, the first, second, and third portions 40, 42, 46 are optionally substantially rougher than the recessed portions 44, 48 according to some embodiments in order to reduce the relative frictional characteristics of the portions 40, 42, 46 relative to the recessed portions 44, 48.

Figure 4:
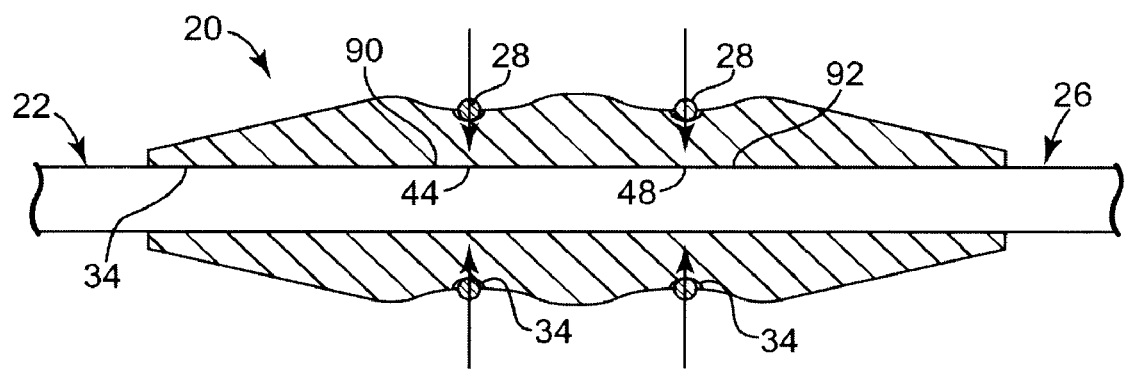
FIG. 4 is a cross-sectional view of the anchoring device of FIG. 2 in a compressed state, according to some embodiments.

FIG. 4 shows the device 20 compressed onto the lead 22 according to some embodiments. Compressing the device 20 onto the lead 22, or transitioning the device 20 from a non-compressed state (FIG. 3) to a compressed state (FIG. 4), includes exerting a compressive force on the device 20 with the fasteners 28. In some embodiments, the fasteners 28 are positioned within the suture grooves 34 and tightened about the device 20 to exert a radial compressive force as designated generally by arrows in FIG. 4.

Upon compression of the device 20, some or all of the inner bore 32 at the recessed portions 44, 48 is deflected inwardly against the lead 22 to contact the sheath 26 of the lead 22 at first and second interfaces 90, 92. In some embodiments, the lead 22 at one or both of the interfaces 90, 92 is formed of at least one of polyurethane and silicone and the anchoring device 20 at one or both of the interfaces 90, 92 is formed of at least one of polyurethane and silicone, although a variety of materials can be suitable according to various applications of the device 20.

The inner bore 32 at the recessed portions 44, 48 has a substantially higher stiction or retention characteristic relative to other portions of the inner bore 32 such that the device 20 has an increased retention force on the lead 22 after having been transitioned to the compressed state. In some embodiments, prior to compression or in a "natural state," the device 20 can be readily positioned along the lead 22 at a desired position. For example, due to the design of the recessed portions 44, 48 only the relatively lower friction portions 40, 42, 46 contact the lead 22 in the non-compressed state to facilitate sliding the device 20 over the lead 22.

Once the device 20 is positioned along the lead 22 at the desired position, the fasteners 28 are tightened and the device 20 is secured to bodily tissue at an anchoring location, for example at or near a corresponding vein entry site of the lead 22 to secure the lead 22 to the bodily tissue.

Figure 5:
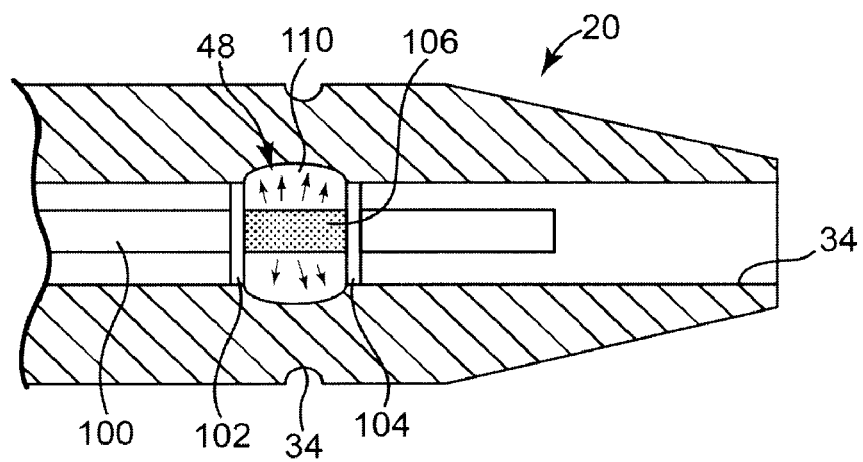
FIG. 5 is illustrative of a method of making the anchoring device of FIG. 2, according to some embodiments.

FIG. 5 schematically illustrates a method of making the anchoring device 20 (shown in cross-section) with an anti-lubricous coating at the recessed portions 44, 48 according to some embodiments. As shown in FIG. 5, a hollow mandrel or other insert 100 including distal and proximal gaskets 102, 104 and a porous section 106 between the gaskets 102, 104 is inserted within the inner bore 34. The porous section 106 is disposed at one of the first and second recessed portions 44, 48, where the porous section 106 is shown at the recessed portion 48 in FIG. 5 for illustrative purposes.

In some embodiments, an anti-lubricous, or friction-enhancing coating 110 (designated generally by arrows in FIG. 5) is sprayed or otherwise flowed from the porous section 106 to coat the recessed portion 48. The gaskets 102, 104 act to help prevent the coating 110 from being deposited elsewhere on the inner bore 34. The insert 100 can then be positioned at the recessed portion 44 with the process repeated to similarly coat the recessed portion 44. In other embodiment methods of making the device 20, a mandrel (not shown) having one or more portions with a mirror finish corresponding to one or both of the first and second recessed portions 44, 48 is used during a molding operation to provide the recessed portions 44, 48 with a very smooth or ultra smooth finish. The mandrel optionally has a substantially rougher portion adjacent the mirror finish portion. In some embodiments, a mirror finish corresponds to a surface roughness of about 15 microinches Ra or less.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An anchoring device for anchoring a medical lead implanted in a patient, the anchoring device comprising:
a substantially elongate, hollow, tubular, and elastically compressible body, the body having a longitudinal axis;
a suture groove formed circumferentially about the tubular body for receiving a suture; and
an inner bore extending through the tubular body and configured to accommodate a medical lead extending through the inner bore, the inner bore forming a recessed portion having an inner bore diameter, and a surrounding portion having an inner bore diameter adjacent the recessed portion, the recessed portion having an inner surface area having a friction enhancing characteristic relative to the surrounding portion;
wherein the recessed portion has a relaxed configuration in which the inner bore diameter of the recessed portion is greater than the inner bore diameter of the surrounding portion and that permits the anchoring device to be slid onto the medical lead and a contact configuration in which the inner surface area of the recessed portion is configured to frictionally engage the medical lead so as to secure the medical lead relative to the anchoring device, the recessed portion moving from the relaxed configuration to the contact configuration in response to a compressive force applied via a suture disposed within the suture groove.

2. The device of claim 1, wherein the recessed portion is adapted to have increased retention characteristics on a polyurethane sheath of a medical lead.

3. The device of claim 1, wherein the recessed portion includes an uncoated silicone surface for interacting with the medical lead.

4. The device of claim 1, wherein the recessed portion is substantially smoother than the surrounding portion of the inner bore.

5. The device of claim 1, wherein the recessed portion defines a surface roughness of about 15 micro inches Ra or less.

6. The device of claim 1, wherein the recessed portion defines a surface area of at least about 10 square mm.

7. The device of claim 1, wherein the recessed portion has an arcuate shape when viewed in side profile perpendicular to the longitudinal axis of the body.

8. The device of claim 1, wherein the recessed portion includes a friction-enhancing coating.

9. The device of claim 1, wherein the recessed portion is located at least partially under the suture groove.

10. The device of claim 1, wherein the recessed portion has a greater stiction characteristic than the surrounding portion.

11. The device of claim 1, further comprising an additional suture groove.

12. The device of claim 11, wherein the inner bore further comprises an additional recessed portion.

13. The device of claim 12, wherein the additional recessed portion is located at least partially under the additional suture groove.

14. The device of claim 1, wherein the recessed portion has a surface roughness that is substantially less than the surrounding portion.

15. The device of claim 1, wherein the compressible body is formed of silicone.

16. The device of claim 1, wherein the recessed portion is substantially circular in transverse cross-section and substantially arcuate in longitudinal cross section.

17. An implantable lead system comprising:
   an implantable lead; and
   an anchoring device disposed on the implantable lead, the anchoring device comprising:
   a substantially elongate, hollow, tubular, and elastically compressible body, the body having a longitudinal axis;
   a suture groove formed circumferentially about the tubular body for receiving a suture; and
   an inner bore extending through the tubular body and configured to accommodate the implantable lead extending through the inner bore, the inner bore forming a recessed portion having an inner diameter, and a surrounding portion having an inner bore diameter adjacent the recessed portion, the recessed portion having an inner surface area having a friction enhancing characteristic relative to the surrounding portion;
   wherein the recessed portion has a relaxed configuration in which the inner diameter of the recessed portion is greater than the inner diameter of the surrounding portion and that permits the anchoring device to be slid onto the implantable lead and a contact configuration in which the inner surface area of the recessed portion is configured to frictionally engage the implantable lead so as to secure the implantable lead relative to the anchoring device, the recessed portion moving from the relaxed configuration to the contact configuration in response to a compressive force applied via a suture disposed within the suture groove.

18. The implantable lead system of claim 17, further comprising a fastener received in the suture groove of the anchoring device and compression the recessed portion against the implantable lead.

19. The implantable lead system of claim 18, wherein a portion of the implantable lead at a location where the recessed portion is compressed against the implantable lead is formed of at least one of polyurethane and silicone and a portion of the anchoring device at the same location is formed of at least one of polyurethane and silicone.

* * * * *